United States Patent
Siefert et al.

(10) Patent No.: US 6,270,799 B1
(45) Date of Patent: Aug. 7, 2001

(54) MEDICAMENT FORMULATION WITH A CONTROLLED RELEASE OF AN ACTIVE AGENT

(75) Inventors: Hans-Martin Siefert, Wuppertal; Patrick Bosché, Odenthal; Heino Stass, Köln; Stefan Kettelhoit, Solingen; Tobias Laich, Köln, all of (DE)

(73) Assignee: Bayer Aktiengesellscahft, Leverkusen (DE)

( * ) Notice: Subject to any disclaimer, the term of this patent is extended or adjusted under 35 U.S.C. 154(b) by 0 days.

(21) Appl. No.: 09/508,868

(22) PCT Filed: Sep. 15, 1998

(86) PCT No.: PCT/EP98/05842

§ 371 Date: Mar. 17, 2000

§ 102(e) Date: Mar. 17, 2000

(87) PCT Pub. No.: WO99/15172

PCT Pub. Date: Apr. 1, 1999

(30) Foreign Application Priority Data

Sep. 25, 1997 (DE) .............................................. 197 42 243

(51) Int. Cl.[7] .............................. A61K 9/28; A61K 9/14; A61K 9/16; A61K 47/32
(52) U.S. Cl. ......................... 424/474; 424/488; 424/489; 424/494; 514/772.4
(58) Field of Search ..................... 514/58, 300, 772.4; 424/474, 488, 489, 494

(56) References Cited

U.S. PATENT DOCUMENTS

| | | | |
|---|---|---|---|
| 3,485,770 | 12/1969 | Borchert et al. | 252/429 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 3,977,404 | 8/1976 | Theeuwes | 128/260 |
| 4,002,173 | 1/1977 | Manning et al. | 128/296 |
| 4,036,227 | 7/1977 | Zaffaroni et al. | 128/260 |
| 4,207,893 | 6/1980 | Michaels | 128/260 |
| 4,857,336 | 8/1989 | Khanna et al. | 424/473 |
| 4,990,517 | 2/1991 | Petersen et al. | 514/300 |
| 4,992,278 | 2/1991 | Khanna | 424/473 |
| 5,473,103 | 12/1995 | Domb et al. | 562/509 |
| 5,520,920 | 5/1996 | Castillo et al. | 424/405 |
| 5,849,752 | * 12/1998 | Grunenberg et al. | 514/300 |
| 5,874,418 | * 2/1999 | Stella et al. | 514/58 |

FOREIGN PATENT DOCUMENTS

| | | | |
|---|---|---|---|
| 0350733 | 1/1990 | (EP) | C07D/401/04 |
| 0550903 | 7/1993 | (EP) | C07D/471/04 |
| 0635272 | 1/1995 | (EP) | A61K/47/34 |
| 0780390 | 6/1997 | (EP) | C07D/471/04 |
| 0624959 | 1/1994 | (JP) | A61K/9/00 |
| 9640080 | 12/1996 | (WO) | A61K/9/36 |

OTHER PUBLICATIONS

Theeuwes, F., "Elementary Osmotic Pump", J. Pharm. Sci., 64(12): 1987–1991 (Dec. 1975).

A.M. Martel, P.A. Leeson, J. Castañer. Prous Science Publishers, Drugs of the Future, 22(2): 109:113 (1997).

Harder, S.; Fuhr, U.; Beermann, D.; and Staib, A.H., "Ciprofloxacin absorption in different regions of the human gastrointestinal tract. Investigations with the hf–capsule", Br. J. Clin. Pharmac., 30: 35–39 (1990).

The United States Pharmacopeia USP 23(711): 1791–1793 (1995).

Santus, G.; Baker, R.W., "Osmotic drug delivery: a review of the patent literature", Journal of Controlled Release, 35: 1–21 (1995).

Boxenbaum, H., "Pharmacokinetic Determinants in the Design and Evaluation of Sustained–Release Dosage Forms", Pharma. Res., 15: 82–88 (1984).

Stass, H.H.; Dalhoff, A.; Kubitza, D.; Ahr, G., "Bay 12–8039, A New 8–Methoxy–quinolone: First Pharmacokinetic (PK) Results in Healthy Male Volunteers", Abstracts of the 36th ICAAC, F24 p. 104, New Orleans (1996).

* cited by examiner

Primary Examiner—Thurman K. Page
Assistant Examiner—Blessing Fubara
(74) Attorney, Agent, or Firm—Jerrie L. Chiu

(57) ABSTRACT

The invention relates to drug formulations which comprise 1-cyclopropyl-7-([S,S]-2,8-diazabicyclo[4.3.0]non-8-yl)-6-fluoro-1,4-dihydro-8-methoxy-4-oxo-3-quinolonecarboxylic acid and/or pharmaceutically tolerable salts thereof and/or hydrates thereof as active compound which release the active compound they contain at a defined release rate.

15 Claims, 1 Drawing Sheet

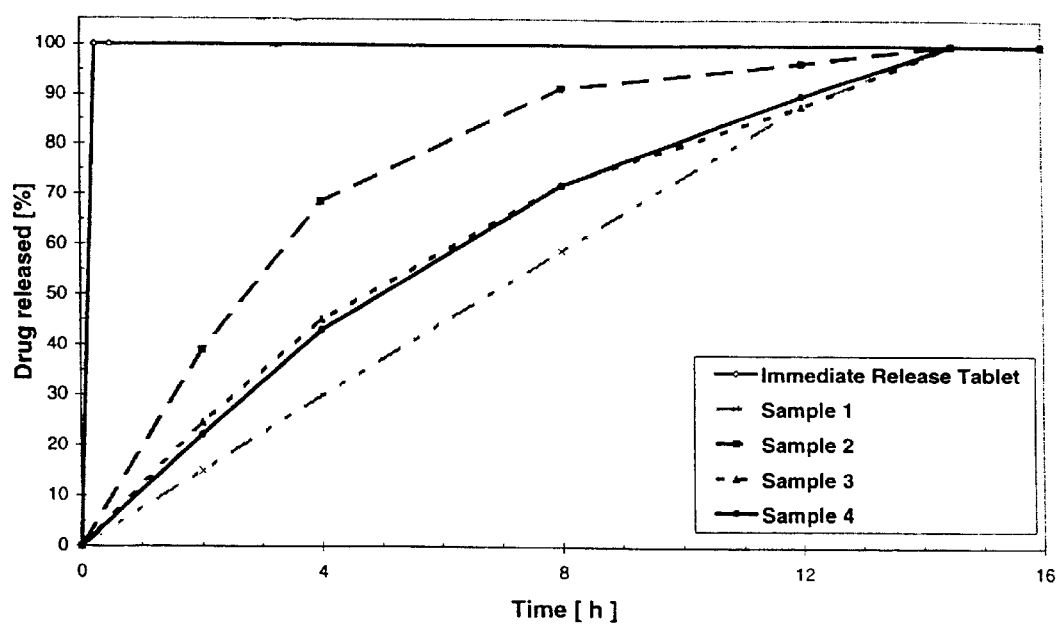
Figure 1: Comparison of the release of active compound from formulations according to Comparative Example 1 (rapid release) and examples 1-4 (controlled release)

MEDICAMENT FORMULATION WITH A CONTROLLED RELEASE OF AN ACTIVE AGENT

The invention relates to drug formulations which comprise 1-cyclopropyl-7-([S,S]-2,8-diazabicyclo[4.3.0]non-8-yl)-6-fluoro-1,4-dihydro-8-methoxy-4-oxo-3-quinolonecarboxylic acid (hereinbelow referred to as compound I) and/or pharmaceutically tolerable salts thereof and/or hydrates thereof as active compound which release the active compound they contain at a defined release rate.

The compound I has the INN (International Non-Proprietary Name) moxifloxacin.

The compound I and/or its salts and/or hydrates is a novel 8-methoxyquinolone having antibacterial action against gram-negative and gram-positive bacteria which is frequently significantly better than that of sparfloxacin and ciprofloxacin (Drugs of the Future 1997, 22 (2): 109/113). EP-A-0 305 733 and also EP-A-0 550 903 describe the preparation of the compound I and also of its pharmaceutically tolerable salts. EP-A-0 780 390 describes a specific crystal modification of the monohydrate hydrochloride of the compound I.

Tablet formulations having delayed and/or controlled release of active compound which contain quinolonecarboxylic acid antibiotics are not well known. JP-A-06 024 959 does admittedly describe an oral drug which comprises ciprofloxacin-hydrochloride, but the preparation of administration forms which release the active compound throughout the entire gastrointestinal tract is virtually impossible for cyprofloxacin-hydrochloride. The reason for this is the absorption behaviour of ciprofloxacin in the colon (S. Harder, U. Fuhr, D. Beermann, A. H. Staib, "Ciprofloxacin absorption in different regions of the human gastrointestinal tract. Investigations with the hf-capsule", Br. J. clin. Pharmac. 30, (1990), 35–39). The data found by Staib and Fuhr for humans confirm the present data from animal experiments showing that cyprofloxacin-hydrochloride is only absorbed to a very small degree from the colon. Because of this, the great majority of the known ciprofloxacin formulations having delayed release of active compound are drug formulations which cannot be administered perorally. Thus, U.S. Pat. No. 5,473,103 describes ciprofloxacin-comprising implants. Furthermore, U.S. Pat. No. 5,520,920 describes an eye drug formulation having delayed release of active compound. Likewise, only a parenteral formulation, which completely releases the active compound in approximately 3 hours (EP-A-0 635 272), is described for the known quinolonecarboxylic acid antibiotic ofloxacin.

EP-A-0 350 733 mentions the possibility of formulating the active compounds described in this document in compositions which release, optionally delayed, the active compound only or preferably in a certain part of the intestinal tract. However, concrete formulations having delayed release of active compound of the compounds disclosed therein are not described. The concrete tablet formulation which is described in EP-A-0 350 733 for the compound of example 1 mentioned therein is a rapid-release formulation which releases the active compound usually within approximately half an hour. The pharmaceutical formulations of the hydrochloride monohydrate of the compound I described in EP-A-0 780 390 are likewise formulations having rapid release of active compound which usually lead to the release of active compound within approximately half an hour.

However, after administration of such a rapid-release tablet formulation, the concentrations of the active compound in the blood are subject to high fluctuations when the drug formulation is administered repeatedly, as is customary in therapies. After peroral administration, for example, of the above mentioned formulations having rapid release of active compound, the maximum concentrations of the active compound in the blood are reached within 4 hours. They then decrease considerably until the next administration. Thus, multiple administration of tablet formulations having rapid release of active compound result in high fluctuations of the concentration of the active compound in the blood. However, in some cases high concentrations of the active compound in the blood which occur after administration of a tablet formulation having rapid release of active compound are undesired, since, for example, side effects may also occur more frequently. Additionally, it is desirable in some cases to maintain the concentrations of the active compound in the blood at a higher level over a prolonged period.

Such a drug formulation having delayed release moreover offers a number of fundamental advantages, such as less frequent administration, which improves patient compliance. Additionally, advantages may be achieved in the case of certain infections where even longer-lasting active compound levels than with a rapid-release tablet are important. Altogether, a drug formulation having delayed release offers greater possibilities to adjust the level of active compound to match the specific infection and the sensitivity of the patient.

It was therefore the object of the present invention to develop a drug formulation of the compound I and pharmaceutically tolerable salts thereof and/or their hydrates which meets the requirements described above. Initially, therefore, the inventors intensively studied the absorption behaviour of the hydrochloride of the compound I (hereinbelow referred to as compound II) and found, very surprisingly, that, for example in contrast to the above mentioned ciprofloxacin, the compound II is also absorbed in the lower sections of the intestine (colon, rectum). Only this surprising absorption behaviour of moxifloxacin, which is different from known quinolonecarboxylic acid antibiotics, opens up any possibility of developing a retard formulation of moxifloxacin.

During further intensive investigations, it was then also surprisingly possible to develop drug formulations which release the active compound over a prolonged period in the entire gastro-intestinal tract, and finally to develop drug formulations having certain release profiles which are suitable for solving the above-described problems of the prior art.

The present invention, accordingly, provides a drug formulations having controlled release of active compound, which comprises 1-cyclopropyl-7-([S,S]-2,8-diazabicyclo [4.3.0]non-8-yl)-6-fluoro-1,4-dihydro-8-methoxy-4-oxo-3-quinolone-carboxylic acid or pharmaceutically tolerable salts and/or hydrates thereof and which has an average release between 80% in 2 hours and 80% in 16 hours and an initial release of less than 60% of the active compound in the first hour of release.

To determine the initial and average release according to the definition of the invention, the drug formulations of the present invention are tested in "Apparatus 2" of USP XXIII (The United States Pharmacopeia USP XXIII 1995, pages 1791–1792). The test medium used is 900 ml of 0.1 molar hydrochloric acid or a phosphate buffer with pH 7.4. The rotational speed of the stirrer is 50 revolutions per minute. Samples are passed through an 8 μm filter, and their active compound content is determined. The amount of active compound which is determined in this manner as being dissolved is converted into per cent by weight of the amount of active compound employed.

The drug formulation having controlled release of active compound of the present invention preferably has an average release of 80% in the period between 4 and 14 hours (80% in 4 hours and 80% in 14 hours).

In even more preferred embodiment of the drug formulation having controlled release of active compound of the present invention, the formulation has an average release of 80% in the period between 7 hours and 13 hours and an initial release of less than 50% of the active compound in the first hour of release.

The drug formulation having controlled release of active compound of the present invention can be formulated in such a manner that a relatively high initial release in the first hour of 30 to 60% of the active compound or a relatively low initial release in the first hour of 0 to 30% of the active compound are obtained.

In a preferred embodiment of the drug formulation having controlled release of active compound with a relatively high initial release between 45 and 55% of the active compound in the first hour of release, the formulation has an average release of 80% in the period from 8 hours to 12 hours.

In a preferred embodiment of the drug formulation having controlled release which has a relatively low initial release between 0 and 20% of the active compound in the first hour of release, this formulation is characterized by an average release of 80% in the period between 8 hours and 12 hours.

The drug formulations described above having controlled release of active compound are present, for example, in the form of diffusion-controlled pellets. These diffusion-controlled pellets comprise, for example, neutral pellets onto which a mixture of the active compound with customary binders and thickeners, if appropriate together with customary auxiliaries and carriers, as defined, for example, below, is applied and which are subsequently coated with a diffusion coat comprising plasticizers, or they comprise an active-compound-containing core which is coated with a diffusion coat.

Preferred binders and thickeners are hydroxypropylmethylcellulose or polyvinylpyrrolidone. It is also possible to employ other natural, synthetic or semi-synthetic polymers, such as, for example, methylcellulose, hydroxypropylcellulose, sodium carboxymethylcellulose, polyacrylic acids, polyvinyl alcohols or gelatin.

A particularly suitable diffusion coat is ethylcellulose, commercially available, for example, as aqueous dispersion under the name Aquacoat® or Surelease®. However, other materials such as acrylates (Eudragit®), cellulose acetate and cellulose acetate butyrate can also be used.

Suitable plasticizers are, for example, phthalic acid derivatives (for example dimethyl phthalate, diethyl phthalate, dibutyl phthalate), citric acid derivatives (for example triethyl citrate, tributyl citrate, acetyltriethyl citrate), other esters (for example diethyl sebacate, triacetin), fatty acids and derivatives (glycerol monostearate, acetylated fatty acid glycerides, castor oil and other native oils, miglyol), polyols (glycerol, 1,2-propanediol, polyethylene glycol of varying chain length). Furthermore, the nature and amount of plasticizer are adjusted such that the above-defined release according to the invention and the required stability of the pellets is obtained.

The above-defined release is adjusted by controlling the pore size of the diffusion coat and its thickness. Pore formers which can be used to control the pore size are soluble polymers, such as, for example, polyethylene glycols, polyvinylpyrrolidones, hydroxypropylmethylcelluloses, carboxymethylcelluloses or salts thereof, methyl celluloses, dextrins, maltodextrins, cyclodextrins, dextrans or other soluble compounds, such as, for example, salts (common salt, potassium chloride, ammonium chloride, etc.), urea, sugars (glucose, sucrose, fructose, lactose, etc.), sugar alcohols (manitol, sorbitol, lactitol, etc.). The proportion of the pore former in the coating material is 0 to 50% (w/w), preferably 0 to 25%, or 5 to 25% (w/w) (w=weight).

For the pellets, it is especially important to use a certain weight ratio of active-compound-coated pellets to the diffusion membrane and also a certain ratio of diffusion coat to the amount of plasticizer.

During coating and subsequent thermal treatment, some of the plasticizer employed may evaporate. The amount of coat according to the invention of diffusion coat has to be modified when the marginal parameters are changed. Thus, for example, a large amount of coat is required when the desired release rate is reduced, the amount of pore former is increased or when, in the case of certain plasticizers, the proportion of plasticizer is reduced. A lower amount of coat is required when the desired release rate is increased, the amount of pore former is reduced or when, in the case of certain plasticizers, the proportion of plasticizer is increased.

The diffusion pellets according to the invention can be prepared, for example, by suspending or dissolving the active compound in water, and thickening it with a concentrated hydroxypropylmethylcellulose solution. The resulting suspension is applied to the neutral pellets by spraying in a fluidized-bed unit. This is followed by coating of the pellets with a diffusion membrane by spraying on, for example, an aqueous ethylcellulose dispersion, preferably in a fluidized-bed unit, which contains a suitable, physiologically tolerable plasticizer. The pellets are subsequently subjected to thermal treatment at temperatures of from 50 to 125° C., preferably from 60 to 110° C. Higher temperatures during the thermal treatment result in lower amounts of coating being sufficient for obtaining the release according to the invention, and in the pellets formed being physically more stable on storage. The thickness of the diffusion membrane, the type and the amount of plasticizer and the pellet size are chosen so that a release rate of 80% of the compound I or II in 2 to 16 hours results and less than 60% of the dose are released within the first hour. The amount of pellets corresponding to a daily dose of, for example, 400 mg of the compound I (Betaine form) is filled into a hard gelatin capsule.

In addition to the described coating of neutral pellets, other methods of pellet preparation, such as the extrusion/spheronizer process, rotor granulation or fluidized-bed agglomeration, are also feasible.

In the case of coated neutral pellets, a diffusion pellet thus comprises 10 to 50% (w/w) (w=weight) of neutral pellets (for example sucrose and binder or citric acid), preferably 10 to 40% (w/w) of neutral pellets, onto which are applied 10 to 85% (w/w) of active compound layer, preferably 30 to 75% (w/w). For high doses of active compound ($\geq$400 mg of betaine per individual dose), particular preference is given to 10 to 30% (w/w) of neutral pellets onto which are applied 50 to 85% (w/w) of active compound layer. The active compound layer comprises 70 to 99.5% (w/w) of active compound and 0.5 to 30% (w/w) of binder, preferably 80 to 99.5% (w/w) of active compound and 0.5 to 20% (w/w) of binder. For high doses of the active compound, particular preference is given to 90 to 99.5% (w/w) of active compound and 0.5 to 10% (w/w) of binder.

The pellets obtained in this manner are coated with the diffusion coat or the diffusion layer, preferably in an amount of 5 to 40% (w/w), which, based on the amount of coat, comprises 40 to 90% (w/w) of film former (film-forming polymer, for example ethylcellulose (Aquacoat® or Surelease®), acrylate (Eudragit®), cellulose acetate, cellulose acetatate butyrate), preferably 50 to 85% (w/w), particularly preferably 60 to 85% (w/w), of pore former (soluble polymers, such as, for example, polyethylene glycols, polyvinylpyrrolidones, hydroxypropylmethylcelluloses, carboxymethyl-celluloses or salts thereof, methylcelluloses, dextrins, maltodextrins, cyclodextrins, dextrans or other soluble compounds, such as, for example, salts (common salt, potassium chloride, ammonium chloride, etc.), urea, sugar (glucose, sucrose, fructose, lactose, etc.), sugar alcohols (manitol, sorbitol, lactitol, etc.) in the range from 0 to 50% (w/w), preferably 0 to 35% (w/w), particularly preferably 0 to 25% (w/w) or 5 to 25% (w/w), and plasticizer in the range of 5 to 50% (w/w), preferably 5 to 35% (w/w), particularly preferably 10 to 35% (w/w).

In the case of coated active compound pellets, a diffusion pellet comprises 50 to 95% (w/w) of active compound pellets, preferably 60 to 95% (w/w). For high doses of the active compound ($\geq$400 mg of betaine per individual dose), particular preference is given to 70 to 95% (w/w) of active compound pellets. These active compound pellets comprise 70 to 99.5% (w/w) of active compound and 0.5 to 30% (w/w) of binder, particularly preferably 80 to 99.5% (w/w) of active compound and 0.5 to 20% (w/w) of binder. For high doses of the active compound, particular preference is given to 90 to 99.5% (w/w) of active compound and 0.5 to 10% (w/w) of binder, and also, if appropriate, further additives (microcrystalline cellulose, thermoplastic polymer, other pharmaceutically usual auxiliaries). The pellets obtained in this manner are coated with the diffusion coat or the diffusion layer in an amount of 5 to 50% (w/w), which, based on the amount of coat, comprises 40 to 90% (w/w) of film former (film-forming polymer, for example ethylcellulose (Aquacoat® or Surelease®), acrylate (Eudragit®), cellulose acetate, cellulose acetatate butyrate), preferably 50 to 85% (w/w), particularly preferably 60 to 85% (w/w), of pore former (soluble polymers, such as, for example, polyethylene glycols, polyvinylpyrrolidones, hydroxypropylmethylcelluloses, carboxymethylcelluloses or salts thereof, methylcelluloses, dextrins, maltodextrins, cyclodextrins, dextrans or other soluble compounds, such as, for example, salts (common salt, potassium chloride, ammonium chloride, etc.), urea, sugar (glucose, sucrose, fructose, lactose, etc.), sugar alcohols (manitol, sorbitol, lactitol, etc.) in the range from 0 to 50% (w/w), preferably 0 to 35% (w/w), particularly preferably 0 to 25% (w/w) or 5 to 25% (w/w), and plasticizer in the range of 5 to 50% (w/w), preferably 5 to 35% (w/w), particularly preferably 10 to 35% (w/w).

In a further embodiment of the drug formulation having controlled release of active compound of the present invention, formulations are used which comprise the active compound in a matrix of a water-swellable polymer. These formulations are preferably present in the form of a tablet.

These so-called matrix formulations expediently comprise from 30 to 70% by weight, preferably 40 to 60% by weight, of the active compound.

The proportion by weight of the matrix of the water-soluble polymer is expediently from 30 to 50% by weight, preferably 30 to 40% by weight. Preference is additionally given to drug preparations according to the invention in the form of erosion tablets. These tablets are characterized in that they contain, in addition to customary auxiliaries and carriers and tabletting auxiliaries, a certain amount of water-swellable hydrogel-forming polymers, where these polymers have to have a viscosity of at least 15, preferably at least 50 mPa.s (measured as a 2% strength aqueous solution at 20° C.).

Customary auxiliaries and carriers are, for example, lactose, microcrystalline cellulose, manitol or calcium phosphate. These are expediently present in an amount of 0 to 50% by weight, preferably 10 to 40% by weight, particularly preferably 20 to 40% by weight.

Customary tabletting auxiliaries are, for example, magnesium stearate, talc or finely divided silica (Aerosil®). In the case of magnesium stearate, these are expediently present in an amount of from 0.5 to 1.5% by weight, and in the case of finely divided silica expediently in an amount of from 0.1 to 0.5% by weight.

Preferred water-soluble, hydrogel-forming polymers are hydroxypropylcelluloses, hydroxypropylmethylcelluloses (HPMC), methylcelluloses, carboxymethylcellulose, alginates, galactomannans, polyacrylic acids, polymethacrylic acids or copolymers of methacrylic acid and methyl methacrylate, guar gum, agar, pectin, tragacanth gum, gum arabic, xanthan gum, or mixtures of these substances.

Particular preference is given to the use of HPMC.

Here, the erosion tablets according to the invention should preferably contain at least 10% by weight, based on the weight of a tablet, of a hydroxypropylmethylcellulose type whose viscosity (measured as a 10% strength aqueous solution at 20° C.) is at least 15, preferably at least 50, mPa.s.

The drug formulation which comprises the active compound in a matrix of a water-swellable polymer is prepared by mixing and directly tabletting the active compound, the polymer and suitable auxiliaries and carriers (as described above) and also customary tabletting auxiliaries (as described above). Furthermore, it is possible to granulate the active compound, the water-swellable polymer and suitable carriers in a fluidized bed. The amount and the viscosity of the water-swellable polymer is chosen so that tablets having the average release rate and initial release described above result. The dry granules are sieved, mixed with a lubricant, such as, for example, magnesium stearate, and tabletted. The tablet is, if appropriate, additionally coated.

In a further embodiment, the drug formulation having controlled release of active compound of the present invention is an osmotic drug release system. Such osmotic drug release systems are known in principle in the prior art and are discussed in detail, for example, in Richard W. Baker, "Osmotic Drug Delivery: A Review of the Patent Literature", Journal of Controlled Release 35 (1995) 1–21. The drug formulation as osmotic drug release system preferably comprises a) a core which contains the active compound, optionally a hydrophilic polymeric swelling agent and optionally a water-soluble substance for inducing osmosis, and b) a shell which is water-permeable and impermeable for the components of the active-compound-containing core, c) an opening through the shell b) for the transport of the components contained in the core into the surrounding aqueous body liquid.

This specific osmotic drug release system is described in principle in the prior art, for example in DE-A-2 328 409 or U.S. Pat. No. 3,845,770. For the materials of the shell, reference is made to EP-A-0 277 092 and U.S. Pat. No. 3,916,899 and U.S. Pat. No. 3,977,404, which are mentioned in this document.

For suitable hydrophilic polymeric swelling agents, reference is made, for example, to the polymeric swelling agents mentioned in EP-A-0 277 092 and WO 96/40080. It is possible to use, for example, ethylene oxide homopolymers (polyethylene glycol) having various degrees of polymerization, which are known under the name Polyox® having molecular weights between 100,000 and 8,000,000, and also to vinylpyrrolidone/vinyl acetate copolymers and other water-swellable polymers mentioned in U.S. Pat. No. 3,865,108, U.S. Pat. No. 4,002,173 and U.S. Pat. No. 4,207,893.

Water-soluble substances for inducing osmosis are in principle all water-soluble substances whose use in pharmacy is conceivable, for example those mentioned as water-soluble auxiliaries in the pharmacopeias or in "Hager's Handbuch der Pharmazeutischen Praxis, 1990–1995, Springer Verlag", and also in Remington's Pharmaceutical Sciences. Since the compound I and/or its salts and/or hydrates have a relatively high water solubility (approximately 24 g/liter), the active compound itself is also osmotically active. This is taken into consideration in the formulation of the osmotic drug system. Further specific water-soluble substances are salts of inorganic or organic acids or non-ionic organic substances having high water solubility, such as, for example, carbohydrates such as sugars, etc. How to produce an opening in the shell of the tablet is known per se in the prior art and described, for example, in the U.S. Pat. Nos. 3,845,770 and 3,916,899.

The above-described average release and the initial release of the drug formulation having controlled release of active compound of the present invention are adjusted by the nature and the amount of the semi-permeable material which forms the shell, by the nature and the amount of the hydrophilic polymeric swelling agent which is optionally present, and by the optionally present water-soluble substance for inducing osmosis.

The drug formulations of the invention expediently comprise, based on 1-cyclopropyl-7-([S,S]-2,8-diazabicyclo[4.3.0]non-8-yl)-6-fluoro-1,4-dihydro-8-methoxy-4-oxo-3-quinolonecarboxylic acid, 200 to 800 mg, preferably 400 to 600 mg, of active compound.

The drug formulation having controlled release of active compound of the present invention is preferably a formulation where, at the same dosage, the maximum blood level ($c_{max}$) is lower than the value $c_{max}$ of a drug formulation with rapid release, as described in example 7 of EP-A-0 780 390, and where the peak trough fluctuation PTF [%] is lower than the corresponding PTF value of the formulation of example 7 according to EP-A-0 780 390.

$$PTF = c_{max} - c_{min}/c_{av,\tau}$$

$c_{min}$: minimum concentration of the active compound in blood, plasma or serum $c_{av,\tau}$: average steady state concentration calculated from the plasma concentration/time data after single administration or after the first dosage interval ($\tau$) after multiple administration.

The determination of PTF is described in H. Boxenbaum, "Pharmacokinetic determinants in the design and evaluation of sustained release dosage forms", Pharm. Res., 15, 82–88 (1984).

The blood levels are determined as described in H. Stass, A. Dalhoff, D. Kubitza, "BAY 12-8039, A new 8-Methoxy-Quinolone: First pharmacokinetic results in healthy male volunteers", Proc. of 36th ICAAC, New Orleans, 1996, F024, page 104.

EXAMPLES

Comparative Example 1

Rapid-release Tablet Corresponding to the Prior Art, According to Example 7 of EP-A-0 780 390

Composition:

| | |
|---|---|
| Compound II (hydrochloride) | 436.8 mg |
| Microcrystalline cellulose | 61.8 mg |
| Maize starch | 31.8 mg |
| Croscarmellose sodium | 3.6 mg |
| Magnesium stearate | 8.0 mg |

The tablet was prepared analogously to Example 7 of EP-A-0 780 390.

Example 1

Matrix Tablet

A matrix tablet has the following composition:

| | |
|---|---|
| Compound II (hydrochloride) | 436.8 mg |
| HPMC 90 SH 100 | 191.0 mg |
| Magnesium stearate | 8.0 mg |
| Iron oxide | 0.3 mg |
| Titanium dioxide | 2.7 mg |
| Polyethylene glycol 4000 | 3.0 mg |
| HPMC 15 cP | 9.0 mg |

Compound II (hydrochloride), HPMC 90 SH 100 and magnesium stearate are mixed dry and compressed to tablets. The tablets are coated with an aqueous suspension containing the iron oxide, the titanium dioxide, the polyethylene glycol 4000 and the HPMC.

Example 2

Matrix Tablet

A matrix tablet has the following composition:

| | |
|---|---|
| Compound II (hydrochloride) | 436.8 mg |
| HPMC 15 cP | 334.0 mg |
| Lactose monohydrate | 334.0 mg |
| Magnesium stearate | 8.2 mg |
| Iron oxide | 0.45 mg |
| Titanium dioxide | 4.05 mg |
| Polyethylene glycol 4000 | 4.5 mg |
| HPMC 15 cP | 13.5 mg |

Compound II (hydrochloride), HPMC 15 cP and lactose are granulated in a fluidized-bed granulator. The magnesium stearate is admixed and this mixture is compressed to tablets. The tablets are coated with an aqueous suspension containing the iron oxide, the titanium dioxide, the polyethylene glycol 4000 and the HPMC.

Example 3

Matrix Tablet

A matrix tablet has the following composition:

| | |
|---|---|
| Compound II (hydrochloride) | 436.8 mg |
| HPMC 15 cP | 334.0 mg |
| Calcium hydrogen phosphate | 334.0 mg |
| Magnesium stearate | 8.2 mg |
| Iron oxide | 0.45 mg |
| Titanium dioxide | 4.05 mg |
| Polyethylene glycol 4000 | 4.5 mg |
| HPMC 15 cP | 13.5 mg |

Compound II (hydrochloride), HPMC 15 cP and calcium hydrogen phosphate are granulated. The magnesium stearate is admixed and this mixture is compressed to tablets. The tablets are coated with an aqueous suspension containing the iron oxide, the titanium dioxide, the polyethylene glycol 4000 and the HPMC.

Example 4

Matrix Tablet

A matrix tablet has the following composition:

| | |
|---|---|
| Compound II (hydrochloride) micronized | 436.8 mg |
| HPMC 50 cP | 109.2 mg |
| Magnesium stearate | 4.0 mg |
| Iron oxide | 0.3 mg |
| Titanium dioxide | 2.7 mg |
| Polyethylene glycol 4000 | 3.0 mg |
| HPMC 15 cP | 9.0 mg |

A comparison of the release of active compound (obtained in accordance with USP XXIII described above) of the formulations of Comparative Example 1 and Examples 1–4 is shown in FIG. 1.

Example 5

Diffusion Pellets

To prepare diffusion pellets, 436 g of the compound II, 17.5 g of polyvinylpyrrolidone 25, 110 g of hydroxypropylmethylcellulose, 18 g of polyethylene glycol 4000, 220 g of ethylcellulose and 21 g of triethyl citrate are employed for preparation and coating of the pellets in a fluidized-bed unit. The pellets are filled into capsules.

Example 6

Osmotic Release System 724.6 g of compound II, 182.5 g of common salt and 82.9 g of microcrystalline cellulose are granulated, the granules are mixed with 10 g of magnesium stearate and this mixture is compressed to tablets (format 5.5 r 9). The tablets are coated with 49.8 g of a mixture of cellulose acetate, polyethylene glycol 3350 and glycerol in an acetone solution. The tablets are perforated in a suitable manner.

What is claimed is:

1. A diffusion-controlled pellet drug formulation having controlled release of an active compound, comprising:
(a) 10–50% by weight of neutral pellet;
(b) 10–85% by weight of a first coat covering said neutral pellet, said first coat comprising a mixture that is 70–99.5% by weight of the active compound, which is selected from 1-cyclopropyl-7-([S,S]-2,8-diazabicyclo[4.3.0]non-8-yl)-6-fluoro-1,4-dihydro-8-methoxy-4-oxo-3-quinolonecarboxylic acid and pharmaceutically tolerable salts and/or hydrates thereof, and 0.5%–30% by weight of a binder; and
(c) 5–40% by weight of a diffusion coat covering said first coat, said diffusion coat comprising 40–90% by weight of a film former, 0–50% by weight of a pore former and 5–50% by weight of a plasticizer;
wherein said drug formulation has an average release of active compound of between 80% in 2 hours and 80% in 16 hours and an initial release that is less than 60% of the active compound in the first hour of release.

2. A diffusion-controlled pellet drug formulation having controlled release of an active compound, comprising:
(a) 50–95% by weight of a core, said core comprising 70–99.5% by weight of the active compound, selected from 1-cyclopropyl-7-([S,S]-2,8-diazabicyclo[4.3.0]non-8-yl)-6-fluoro-1,4-dihydro-8-methoxy-4-oxo-3-quinolonecarboxylic acid and pharmaceutically tolerable salts and/or hydrates thereof, and 0.5–30% by weight of a binder; and
(b) 5–50% by weight of a diffusion coat covering said core, said diffusion coat comprising 40–90% by weight of a film former, 0–50% by weight of a pore former and 5–50% by weight of a plasticizer,
wherein said drug formulation has an average release of active compound of between 80% in 2 hours and 80% in 16 hours and an initial release that is less than 60% of the active compound in the first hour of release.

3. Drug formulation according to claim 1 or 2, wherein said film former is ethylcellulose polymer.

4. Drug formulation according to claim 1 or 2, wherein said binder is selected from hydroxypropylmethylcellulose and polyvinylpyrrolidone.

5. Drug formulation according to claim 1 or 2, wherein said drug formulation is an osmotic drug release system.

6. Drug formulation according to claim 5, comprising:
a) a core which contains the active compound, optionally a hydrophilic polymeric swelling agent and optionally a water-soluble substance for inducing osmosis,
b) a shell of a material which is water-permeable and impermeable for the components of the active-compound-containing core,
c) an opening through the shell b) for the transport of the components contained in the core into the surrounding aqueous body liquid.

7. A matrix system drug formulation having controlled release of an active compound, comprising:
(a) 30–77.3% by weight of the active compound, selected from 1-cyclopropyl-7-([S,S]-2,8-diazabicyclo[4.3.0]non-8-yl)-6-fluoro-1,4-dihydro-8-methoxy-4-oxo-3-quinolonecarboxylic acid and pharmaceutically tolerable salts and/or hydrates thereof,
(b) 20.9–50% by weight of a water-swellable polymer having a viscosity of at least 15 mPa.s (measured as a 2% strength aqueous solution at 20° C.); and
(c) 0–50% by weight of pharmaceutically acceptable auxiliaries and carriers,
wherein said drug formulation has an average release of active compound of between 80% in 2 hours and 80% in 16 hours and an initial release that is less than 60% of the active compound in the first hour of release.

8. Drug formulation according to claim 7, wherein said drug formulation is in the form of a tablet.

9. Drug formulation according to claim 8, wherein the water-swellable polymer is selected from hydroxypropylmethylcellulose and hydroxypropylcellulose.

10. Drug formulation according to claim 1, 2 or 7, in which the initial release in the first hour of release is between 30% and 60% of the active compound.

11. Drug formulation according to claim 1, 2 or 7, in which the initial release in the first hour of release is between 0 and 30% of the active compound.

12. Drug formulation according to claim 1, 2 or 7, having an average release of the active compound of between 80% in 4 hours and 80% in 14 hours.

13. Drug formulation according to claim 12, having an average release of the active compound of between 80% in 7 hours and 80% in 13 hours and an initial release of less than 55% of the active compound in the first hour of release.

14. Drug formulation according to claim 12, in which the average release is between 80% in 8 hours and 80% in 12 hours and the initial release is between 45 and 55% of the active compound in the first hour of release.

15. Drug formulation according to claim 12, in which the average release is between 80% in 8 hours and 80% in 12 hours and the initial release is between 0 and 20% of the active compound in the first hour of release.

* * * * *